United States Patent [19]

Maller et al.

[11] Patent Number: 5,078,758
[45] Date of Patent: Jan. 7, 1992

[54] METHOD AND AN APPARATUS FOR REMOVING FINE-GRAINED PARTICLES FROM A GASEOUS STREAM

[75] Inventors: Samuel G. Maller, Mill Valley; Paul H. Gusciora, Greebrae; David E. Isherwood, Costa Mesa, all of Calif.

[73] Assignee: Chevron Research and Technology Company, San Francisco, Calif.

[21] Appl. No.: 485,105

[22] Filed: Feb. 26, 1990

[51] Int. Cl.$^5$ .............................................. B01D 47/00
[52] U.S. Cl. .......................................... 55/90; 55/270; 55/222; 55/233; 55/257.7; 73/864.81
[58] Field of Search ................. 55/90, 80, 93, 94, 233, 55/222, 270, 257.7; 73/863.12, 863.11, 863.86, 846.81; 208/DIG. 1, 150, 151

[56] References Cited

U.S. PATENT DOCUMENTS

| | | | |
|---|---|---|---|
| 2,523,441 | 9/1950 | McKamy | 55/233 |
| 3,353,799 | 11/1967 | Lions et al. | 55/233 |
| 3,382,649 | 5/1968 | Richmond | 55/84 |
| 3,391,577 | 7/1968 | Friauf et al. | 73/863.12 |
| 3,403,496 | 10/1968 | Ahlander et al. | 55/94 |
| 3,668,825 | 6/1972 | McIlvaine | 73/863.21 |
| 4,854,180 | 8/1989 | Mauleon et al. | 73/863.86 |

FOREIGN PATENT DOCUMENTS 256116  10/1988  Japan ........................................ 55/95

*Primary Examiner*—Bernard Nozick
*Attorney, Agent, or Firm*—Edward J. Keeling; Ernest A. Schaal

[57] ABSTRACT

Method and apparatuses are disclosed for removing fine-grained particles from a gaseous sample stream from fluidized catalytic cracking regeneration unit. In one method, the fine-grained particles are wetted with condensate in a sampling system, then the wetted fine-grained particles are separated from the gaseous stream in a wetted packed column in the sampling system. The separated gaseous sample stream is cooled to remove condensible gases then is reheated. The separated fine-grained particles are kept wetted in the sampling system to prevent fouling of the sampling system, then stream is used as a motive force to return the wetted fine-grained particles to the fluidized catalytic cracking regeneration unit. The stream also is used as a drying agent to at least partially dry the wetted fine-grained particles outside of the sampling system and as a dilution agent to help prevent corrosion.

7 Claims, 1 Drawing Sheet

METHOD AND AN APPARATUS FOR REMOVING FINE-GRAINED PARTICLES FROM A GASEOUS STREAM

FINE-GRAINED PARTICLES FROM A GASEOUS STREAM

The present invention relates to methods and apparatuses for removing fine-grained particles from a gaseous stream, such as a gaseous sample stream from the regeneration unit of a fluid catalytic cracker (FCC). It involves providing a conditioned sample for on-stream analysis from a gaseous sample stream that contains solid particulate matter.

For instance, it can be used to condition a sample of the FCC flue-gas before on-stream analysis for oxygen, carbon monoxide, carbon dioxide, or other gases. When the flue-gas has excess oxygen, the oxygen measurement is the most important. When the flue-gas has very little oxygen, the carbon monoxide and carbon dioxide measurements are equally important.

BACKGROUND OF THE INVENTION

Prior art FCC sample systems often plug with catalyst fines from the flue-gas. The frequency of complete plugging depends upon the type of sample system used. One refinery's sample system worked for two to four weeks at a time, followed by four to eight hours of maintenance. Another refinery's sample system worked for only eight to ten hours at a time.

When the sample system plugs, oxygen measurements read high and carbon monoxide and carbon dioxide measurements read low. This results from air entering the analyzer and diluting the flue gas sample. Under normal conditions, ejectors draw sample through the analyzer, but when the sample system fails, they draw air. While this source of failure can be detected with a low-flow switch on the sample line, the measurement readings will still be inaccurate.

Prior sample systems for gas streams with particulate matter are not reliable when applied to FCC flue-gas sampling. FCC catalyst fines are noted for setting-up like cement when wetted and dried. One very simple sample system uses a small diameter pipe to receive and cool the sample, but this pipe plugs after eight to ten hours of use. Another more complicated system uses a commercially available inertial filter to separate the particles from the gas stream, but it plugs off after less than thirty days.

U.S. Pat. No. 4,259,867 describes an apparatus for sampling pyrolysis gas from a hydrocarbon cracking furnace, but needs condensable materials in the gas stream to wash particles from a packing material. Even the smallest amount of water, condensate, or other polar volatile liquids in a pipe attached to a hot, gas-filled process line may cause cracking of the process piping through stress corrosion as the liquid is vaporized at the metal surface. This risk of stress corrosion prevents us from adapting a commercial version of the pyrolysis-gas sampling apparatus to FCC flue-gas service.

SUMMARY OF THE INVENTION

The present invention involves a method for removing fine-grained particles from a gaseous stream. In that method, the fine-grained particles are wetted, and the wetted fine-grained particles are separated from the gaseous stream. The fine-grained particles can be wetted with water, with cooled condensible gas, or with condensate. Those particles can be separated from the gaseous stream in a wetted packed column.

In one embodiment, fine-grained particles are removed from a gaseous sample stream from a FCC regeneration unit. The fine-grained particles are wetted in a sampling system with condensate, then the wetted particles are separated from the gaseous stream in a wetted packed column in the sampling system. The separated gaseous sample stream is cooled to remove condensible gases and is then heated. The wetted particles are kept wetted in the sampling system to prevent fouling of the sampling system. Steam is used as a motive force to return the wetted particles to the FCC regeneration unit, as a drying agent to at least partially dry those particles outside of the sampling system, and as a dilution agent to help prevent corrosion.

BRIEF DESCRIPTION OF THE DRAWINGS

In order to facilitate the understanding of this invention, reference will now be made to the appended drawings of the preferred embodiments of the present invention. The drawings are exemplary only, and should not be construed as limiting the invention.

DETAILED DESCRIPTION OF THE PREFERRED EMBODIMENTS

Figure 1:
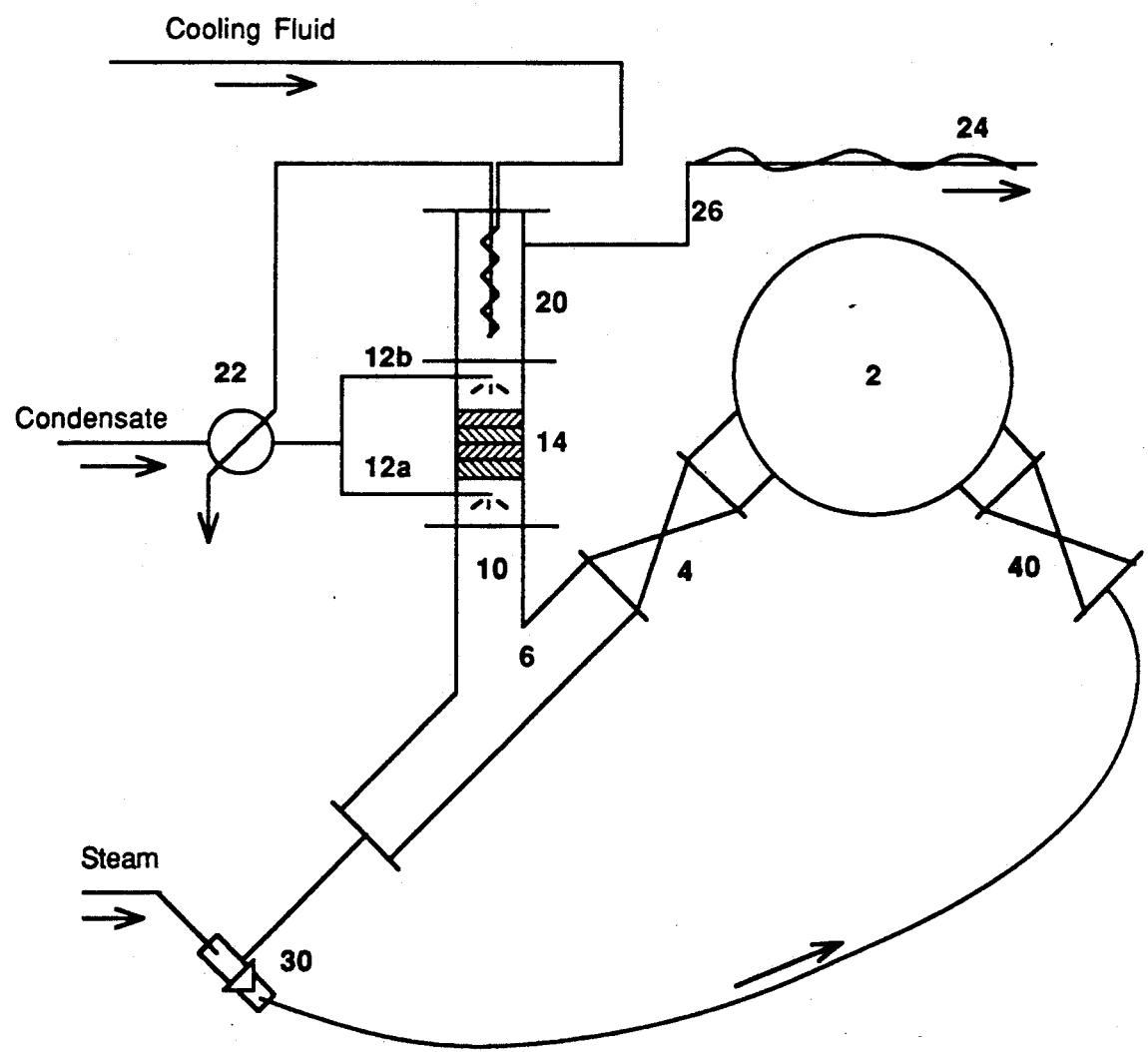
FIG. 1 is a schematic diagram of one embodiment of the present invention.

In its broadest aspect, the present invention involves a method and an apparatus for removing fine-grained particles from a gaseous stream. In that method the fine-grained particles are wetted, then the wetted particles are separated from the gaseous stream.

The apparatus sprays water or other liquid which will be inert to the analyzer, in order to cool the gas and to wet the particles so that they fall out of the gas stream and leave the apparatus through a drain before they can dry. Two or more stages of liquid spray can be used, in which some of the sprays may be directed over a mesh, corrugated packing, or some other packing, in order to effect a more complete separation. The need for a waste stream can be eliminated by attaching an ejector (sometimes called an eductor) that pumps the drain stream back into the original process line or some other convenient point. The gas or liquid that powers the ejector also serves to dilute components of the gas stream which might otherwise corrode the piping. Excess hot gas can be used in the ejector so that most of the liquid in the drain stream will be vaporized before reentry into the process piping.

THE WETTING STEP

In the first step of the present invention, the fine-grained particles are wetted to make them heavier so that they will be easily separated from the gaseous stream. These particles can be wetted by spraying the liquid into the gas stream containing the particles, by spraying the liquid onto packing through which the gas stream flows, or by bubbling the gas and particles up through a pool of liquid. They can be wetted with water, with cooled condensible gas, or with condensate. By "condensate," we mean water which has been condensed from the vapor. The use of condensate is preferred because it has a low tendency to plug the spray nozzles, will not affect the measurements of the analyzers, will not corrode the analyzer, and is devoid of carbon dioxide.

THE SEPARATION STEP

In the second step of the present invention, the wetted fine-grained particles are separated from the gaseous stream. One means of doing this is with a wetted packed column. By "wetted packed column," we mean a mesh, corrugated packing, stoneware packing, or metal shapes enclosed and retained in a section of pipe where the liquid admitted at the top flows down the pipe towards the bottom. Preferably, this embodiment uses two stages of sprays, with the upper spray directed over a packed column.

FCC GASEOUS SAMPLE STREAM

Fine-grained particles can be removed from a gaseous sample stream from a FCC regeneration unit by wetting the particles in a sampling system, separating those wetted particles from the gaseous stream in the sampling system, cooling the separated gaseous sample stream to remove condensible gases, and keeping the wetted particles wetted in the sampling system to prevent fouling of the sampling system.

Preferably, the present invention further comprises heating the cooled gaseous sample stream. Otherwise the water in that gas might condense in the sample line in cold climates and create two-phase flow. Two-phase flow in the sample line will cause faulty measurement readings and other problems. Keeping the gas hot insures that the water will not condense.

Preferably, the wetted fine-grained particles are returned to the FCC regeneration unit. This eliminates the need for other apparatus to handle disposal of the particles. A fluid can provide motive force to return the wetted fine-grained particles to the FCC regeneration unit. Preferably, that fluid is a heated gas that at least partially dries the wetted fine-grained particles outside of the sampling system. An ideal heated gas is steam. Excess steam may be used so that most of the condensate flowing out of the drain is vaporized before returning to the process line.

Referring to FIG. 1, in one embodiment, a gaseous sample stream containing particulate matter flows out of line 2 of a FCC regeneration unit through nozzle and block 4, through sample line 6 and into sampling chamber 10. The gaseous stream is first wetted by spray of condensate from line 12a and then is further wetted in packed column 14, which is wetted by spray of condensate from line 12b. The gaseous stream leaving the top of wetted packed column 14 is cooled by cooler 20 to remove condensible gases and is then heated by the heating lines 24 as the gaseous stream goes through line 26 to the analyzer (not shown). Cooling fluid used in cooler 20 is passed to heat exchanger 22 to cool the condensate. The particulate matter is separated from the gaseous stream in the packed column 14 and flows downward into line 6 until it is pushed by steam from ejector 30 to return the particulate matter through block valve and nozzle 40 to line 2. Steam is used in ejector 30 as a motive force to return the wetted particles to the regeneration unit, as a drying agent to at least partially dry those particles outside of the sampling system, and as a dilution and drying agent to help prevent corrosion.

Advantages of this apparatus are:
it can remain on-stream a long time.
it does not imperil the process piping.
it produces no waste stream.
it permits use of interchangeable, commercially available parts for easy fabrication, maintenance, and repair.

A PREFERRED EMBODIMENT

In one embodiment, flue-gas and catalyst fines are withdrawn through a block valve and nozzle connected to the flue-gas transfer line. The withdrawal nozzles are preferably located above the midpoint of a horizontal section of the FCC flue-gas line. The flue-gas withdrawal rate is critical, because if too much gas is drawn, the process nozzle might overheat. The withdrawal nozzles must be upstream of the flue gas coolers if walnut shells or other cleaning agents are injected to clean those coolers. Also, the withdrawal nozzles must be upstream of the electrostatic precipitators, since those precipitators cause reactions among the gas components that would cause faulty measurement readings.

The withdrawn gas contacts a condensate spray directed downward into a "Y" separating section. Here the gas is cooled and most of the catalyst fines are removed because they have been wetted by contact with the condensate. The catalyst fines fall out and are washed to the bottom of the "Y" by the flow of condensate. As long as sufficient condensate is present, the temperature of the gas will remain well below the saturation temperature of water at the prevailing pressure.

The block valves connected to the withdrawal nozzle may become plugged with fines after the sample system is first installed, or after the system has been turned off for some time, or after the condensate flow has been interrupted. Ancillary piping may be provided to admit high-pressure steam to the sample system so that the nozzles can be blown clean. Also, a solid rod-out device can be installed to break through any solid catalyst that lays in that block valve.

The gas sample contacts more condensate as it passes through a packed column. This packed column encloses a section of stainless-steel packing which fits tightly into the bore of the pipe. Snap-in retaining rings and a spacer hold the packing in place. The packing looks like it has been fabricated from corrugated cardboard laminated together. The corrugations are slanted slightly from the axis of the pipe, and change direction every inch or so.

Here the gas is cooled further, and more catalyst fines are removed. The packing causes the gas to change directions several times as it rises up the column. Vapor passing up through the corrugations is forced to change directions several times as it passes through the corrugations. These direction changes should force wet catalyst particles to impinge on the liquid film running down the packing. This packing has very low holdup, and should be easier to clean than mesh, as it consists largely of almost vertical surfaces. Falling condensate washes catalyst fines down from the packed column and into the "Y" section.

This stream of flue gas, condensate, and catalyst fines passes through a Y, a steam ejector, a line, a block valve and a nozzle, and finally back into the flue-gas line. The return nozzle should be downstream of the withdrawal nozzle. If the return nozzle can be located at a point of low pressure relative to the withdrawal nozzle, the ejector can be eliminated.

The gas sample proceeds up through a water knockout section, where it passes by the outside of a helical cooling coil of stainless-steel tubing. That cooling coil condenses out water and any heavy hydrocarbons. The cleaned gas sample proceeds out the top of the sample system and passes through a Y-type strainer, a check valve, and into steam-traced tubing on its way to the analyzer.

Any cool gas or liquid can be used on the inside of the cooling coil and in the condensate cooler. For instance, on could use process air, process water, cooling water, chilled water, glycol, freon, or any refrigerant. The coolant passes through the cooling coil first, and then into a condensate cooler.

While the present invention has been described with reference to specific embodiments, this application is intended to cover those various changes and substitutions which may be made by those skilled in the art without departing from the spirit and scope of the appended claims.

What is claimed is:

1. A method for removing fine-grained particles from a gaseous sample stream from a fluidized catalytic cracking regeneration unit comprising:
   (a) wetting said fine-grained particles in a sampling system,
   (b) separating said wetted fine-grained particles from said gaseous stream in said sampling system,
   (c) cooling said separated gaseous sample stream to remove condensible gases,
   (d) keeping said wetted fine-grained particles wetted in said sampling system to prevent fouling of said sampling system, and
   (e) returning said wetted fine-grained particles to said fluidized catalytic cracking regeneration unit.

2. A method according to claim 1 wherein a fluid provides motive force to return said wetted fine-grained particles to said fluidized catalytic cracking regeneration unit.

3. A method according to claim 2 wherein said fluid is a heated gas.

4. A method according to claim 3 wherein said heated gas at least partially dries said wetted fine-grained particles outside of said sampling system.

5. A method according to claim 3 wherein said heated gas is steam.

6. A method for removing fine-grained particles from a gaseous sample stream from fluidized catalytic cracking regeneration unit comprising:
   (a) wetting said fine-grained particles in a sampling system with condensate,
   (b) separating said wetted fine-grained particles from said gaseous stream in a wetted packed column in said sampling system,
   (c) cooling said separated gaseous sample stream to remove condensible gases,
   (d) heating said cooled gaseous sample stream,
   (e) keeping said wetted fine-grained particles wetted in said sampling system to prevent fouling of said sampling system,
   (f) using steam as a motive force to return said wetted fine-grained particles to said fluidized catalytic cracking regeneration unit,
   (g) using steam as a drying agent to at least partially dry said wetted fine-grained particles outside of said sampling system, and
   (h) using steam as a dilution agent to help prevent corrosion.

7. An apparatus for producing a gaseous sample stream from a fluidized catalytic cracking regeneration unit comprising:
   (a) a means for sampling, from said fluidized catalytic cracking regeneration unit, a gaseous sample stream containing fine-grained particles;
   (b) a means for wetting said fine-grained particles, wherein the means for wetting said fine-grained particles is adjacent to, and downstream from, the means for sampling a gaseous sample stream;
   (c) a means for separating said wetted fine-grained particles from said gaseous stream, wherein the means for separating said wetted fine-grained particles from said gaseous stream is adjacent to, and downstream from, the means for wetting said fine-grained particles;
   (d) a means for keeping said wetted fine-grained particles wetted in the apparatus to prevent fouling of the apparatus, wherein the means for keeping said wetted fine-grained particles wetted in the apparatus to prevent fouling of the apparatus is adjacent to, and downstream from, the means for separating said wetted fine-grained particles from said gaseous stream;
   (e) a means for cooling said separated gaseous sample stream to remove condensible gases, wherein the means for cooling said separated gaseous sample stream to remove condensible gases is adjacent to, and downstream from, the means for keeping said wetted fine-grained particles wetted in the apparatus to prevent fouling of the apparatus;
   (f) a means for heating said cooled gaseous sample stream, wherein the means for heating said cooled gaseous sample stream is adjacent to and downstream from the means for cooling said separated gaseous sample stream to remove condensible gases; and
   (g) a means for returning said wetted fine-grained particles to said fluidized catalytic cracking regeneration unit, wherein the means for returning said wetted fine-grained particles to said fluidized catalytic cracking regeneration unit is adjacent to, and downstream from, the means for wetting said fine-grained particles.

* * * * *